(12) United States Patent
Chen (10) Patent No.: US 8,487,998 B2
(45) Date of Patent: Jul. 16, 2013

(54) DIGITAL PEEPHOLE VIEWER DEVICE

(75) Inventor: Shih-Che Chen, Taipei (TW)

(73) Assignee: Brinno Incorporated, Taipei (TW)

( * ) Notice: Subject to any disclaimer, the term of this patent is extended or adjusted under 35 U.S.C. 154(b) by 886 days.

(21) Appl. No.: 12/636,173

(22) Filed: Dec. 11, 2009

(65) Prior Publication Data

US 2010/0259618 A1 Oct. 14, 2010

(30) Foreign Application Priority Data

Apr. 9, 2009 (TW) .............................. 98205748 U (51) Int. Cl.
*H04N 7/18* (2006.01)
(52) U.S. Cl.
USPC ......................................... 348/151; 348/143
(58) Field of Classification Search
USPC ................................................. 348/151, 143
See application file for complete search history.

(56) References Cited

U.S. PATENT DOCUMENTS

| 5,191,439 | A | * | 3/1993 | Sumi | 358/447 |
| 5,905,477 | A | * | 5/1999 | Kuwayama et al. | 345/7 |
| 2009/0284600 | A1 | * | 11/2009 | Wang | 348/152 |

* cited by examiner

*Primary Examiner* — Sath V Perungavoor
*Assistant Examiner* — Jeffery Williams
(74) *Attorney, Agent, or Firm* — Schmeiser, Olsen & Watts, LLP (57) ABSTRACT

The present invention discloses a digital peephole viewer device, which integrates with a door lens assembly on a door board to acquire optical images captured by the door lens assembly, converts the optical images into digital images, and then presents the digital images. The digital peephole viewer device of the present invention comprises a housing, an image capture unit, a signal processing unit, a display unit and a connection means. The image capture unit has a first lens to receive the optical images captured by the door lens assembly. The signal processing unit converts the optical images into continuous dynamic digital images. The display unit presents the continuous dynamic digital images. The connection means integrates the housing with the door lens assembly.

14 Claims, 8 Drawing Sheets

DIGITAL PEEPHOLE VIEWER DEVICE

BACKGROUND OF THE INVENTION

1. Field of the Invention

The present invention relates to a digital peephole viewer device, particularly to a digital peephole viewer device, which comprises a housing, an image capture unit, a signal processing unit, a display unit and a connection means, and which can integrate with a door lens assembly to acquire optical images from the door lens assembly, and which transforms optical images into digital images and presents the images on the display unit, and which can further restore the distorted images and present the restored images.

2. Description of the Related Art

No matter whether a residence is in a townhouse, apartment or high-rise building, the door thereof usually has a door lens, whereby the host can watch the visitor or the event outside the house without opening the door.

The conventional door lens assembly comprises a first tube and a second tube. The first tube has a lens. A first end of the second tube has an expanded rim. The first tube is installed at one end of a through-hole of the door board. A second end of the second tube is inserted into the other end of the through-hole and joined to the first tube in a screwing way. The screwing joint of the first and second tubes clamps them to the door board. Then, the user can observe the external situation through the first end of the second tube and the lens.

The conventional door lens assembly has a wide-angle lens. However, the lens is often too small to provide the user with a sufficient vision field. Thus, the user is usually hard to recognize the object outside the door although he watches it attentively, which indeed inconveniences the user very much. Therefore, the conventional door lens assembly has room to improve. There have been many monitoring systems using cameras and displays to solve the abovementioned problems. However, the conventional monitoring systems lack a modularized structure to facilitate convenient installation. Most of the users cannot install a conventional monitoring system by themselves and must rely on professional personnel to install it. Therefore, the conventional monitoring system also has room to improve.

SUMMARY OF THE INVENTION

The primary objective of the present invention is to provide a digital peephole viewer device, which can integrate with a commercially-available door lens assembly without preparing any extra component of the door lens assembly for installation, and which utilizes a digital camera/display technology to provide better recognizability via instantly converting the external images into digital images and presenting the digital images on a larger monitor, whereby the user can watch the visitor and the external situation easily, and whereby the fabrication cost is reduced because the present invention does not need any new mold to fabricate additional components of the door lens assembly.

To achieve the abovementioned objective, the present invention proposes a digital peephole viewer device, which integrates with the door lens assembly to acquire optical images captured by the door lens assembly, converts the optical images into digital images, and then presents the digital images. The digital peephole viewer device of the present invention comprises a housing, an image capture unit, a signal processing unit, a display unit and a connection means. The image capture unit has a first lens to receive the optical images captured by the door lens assembly. The signal processing unit converts the optical images into digital images. The display unit presents the digital images. The connection means integrates the housing with the door lens assembly.

Another objective of the present invention is to provide a digital peephole viewer device, which has a modularized design, whereby the user can easily install the digital peephole viewer device to the existing door lens assembly.

To achieve the abovementioned objective, the present invention proposes a peephole viewer device having a connection means. The connection means includes a seat and a pipe installed in the housing and accommodating the first lens. The seat has a plate, and the plate has a through-hole. A second tube of the door lens assembly is inserted through the through-hole to integrate with a first tube of the door lens assembly in a screwing way. An expanded rim of the second tube is blocked by the perimeter of the through-hole. An annular wall projects from one side of the plate and surrounds the through-holes. The inner surface of the annular wall has several first tenons, and the outer surface of the pipe has several second tenons corresponding to the first tenons. The expanded rim of the second tube clamps the seat to the door board when the first tube and the second tube are coupled to each other in a screwing way. The end of the pipe is inserted into the annular wall, and the first lens is aligned to the end of the second tube, and then the pipe is rotated to an angle where the second tenons of the pipe mate with the first tenons of the annular wall, whereby the housing are coupled to the seat and secured to the door board.

DETAILED DESCRIPTION OF THE INVENTION

1. Technical Characteristics of the Present Invention

Refer to FIGS. 1-8. The present invention proposes a digital peephole viewer device, which integrates a digital camera/display technology with a commercially-available door lens assembly 10 to convert the outdoor optical signals into continuous dynamic digital images, whereby the user can easily observe the outdoor situation. The digital viewer device of the present invention comprises a housing 20, an image capture unit 30, a signal processing unit 40, a display unit 50 and a connection means 60. The connection means 60 joins the housing 20 to the door lens assembly 10 in a door board 1, whereby the digital peephole viewer device receives the optical signals captured by the door lens assembly 10, converts the optical signals into digital images, and instantly presents the outdoor situation.

The image capture unit 30 has a first lens 31 receiving the optical images captured by the door lens assembly 10. The signal processing unit 40 converts the optical images into continuous dynamic digital images of the AVI or MPEG-2 format. The display unit 50 presents the continuous dynamic digital images.

2. Embodiments of the Present Invention 2.1 Door Lens Assembly

Refer to FIGS. 1-3 and FIG. 7. The door lens assembly 10 includes a first tube 11 and a second tube 12, which are coupled to each other in a screwing way. The first tube 11 has a second lens 110 with a wide-angle or fish-eye effect. A first end of the second tube 12 has an expanded rim 120. The first tube 11 is inserted into one end of a through-hole 1a of a door board 1. A second end of the second tube 12 is inserted into the other end of the through-hole 1a and coupled to the first tube 11 in a screwing way.

2.2 Connection Means

Refer to FIGS. 1-3 and FIG. 7. The connection means 60 of the present invention is to couple the housing 20 to the door lens assembly 10, whereby the user can uses the existing door lens assembly 10 to fast and conveniently install the device of the present invention on the door board 1. The connection means 60 includes a seat 61 and a pipe 62 arranged in the housing 20 and accommodating the first lens 31. The seat 61 has a plate 610, and the plate 610 has a through-hole 611. The second tube 12 is inserted through the through-hole 611 to integrate with the first tube 11 in a screwing way. The expanded rim 120 of the second tube 12 is blocked by the perimeter of the through-hole 611. An annular wall 612 projects from one side of the plate 610 and surrounds the through-holes 611. The inner surface of the annular wall 612 has several first tenons 613, and the outer surface of the pipe 62 has several second tenons 620 corresponding to the first tenons 613.

The expanded rim 120 of the second tube 12 clamps the seat 61 to the door board 1 when the first tube 11 and the second tube 12 are coupled to each other in a screwing way. The end of the pipe 62 is inserted into the annular wall 612, and the first lens 31 is aligned to the end of the second tube 12, and then the pipe 62 is rotated to an angle where the second tenons 620 of the pipe 62 mate with the first tenons 613 of the annular wall 612, whereby the housing 20 are coupled to the seat 61 and secured to the door board 1. The end of the pipe 62 is trimmed to be coplanar with the housing 20 so that the housing 20 can closely contact the door board 1. Further, the rim of the pipe 62 has an annular trench to receive the annular wall 612.

2.3 Housing

Refer to FIGS. 1-4. The housing 20 is used to cover and protect the image capture unit 30, the signal processing unit 40 and a power supply unit 70. The housing 20 has a cone-like appearance; the side having a larger area is faced to the door board 1, and the side having a smaller area accommodates a display 51 of the display unit 50. The housing 20 not only has an esthetic appearance but also can securely fix to the door board 1.

Refer to FIGS. 1-4. In a first embodiment of the housing 20, the housing 20 includes a casing 21 having a first opening 22, and a cover 24 is used to cover the first opening 22. The casing 21 accommodates the power supply unit 70. The user can open the cover 24 to replace the power supply unit 70.

Refer to FIGS. 1-4. In a second embodiment of the housing 20, the housing 20 includes a casing 21 having a second opening 23. The display 51 of the display unit 50 is installed in the second opening 23, and a transparent plate 25 is used to cover the second opening 23 and protect the display 51.

Figure 1:
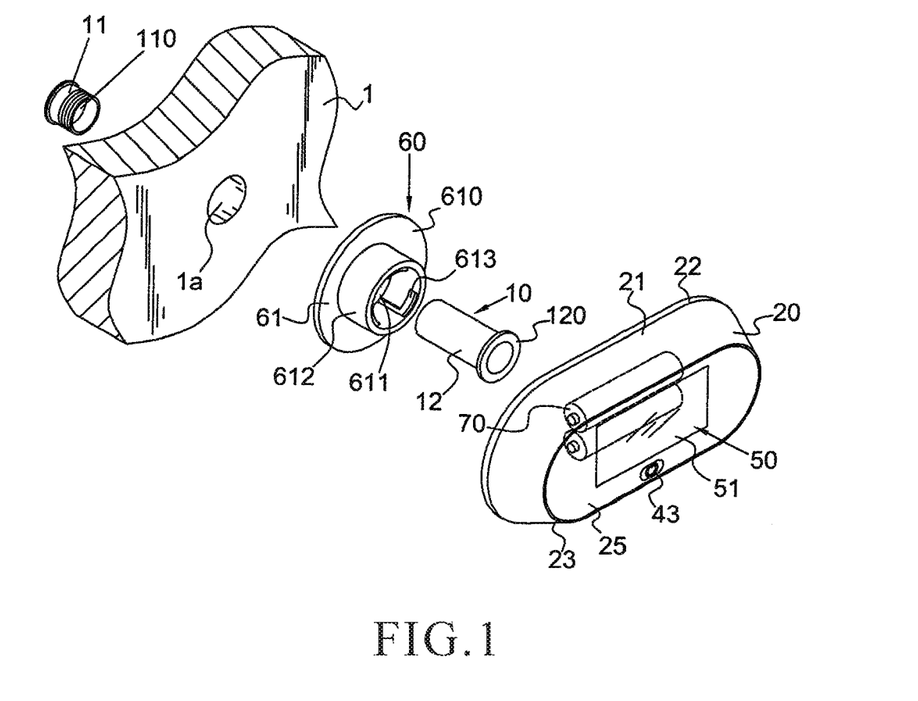
FIG. 1 is a perspective exploded view schematically showing a digital peephole viewer according to the present invention.
Figure 2:
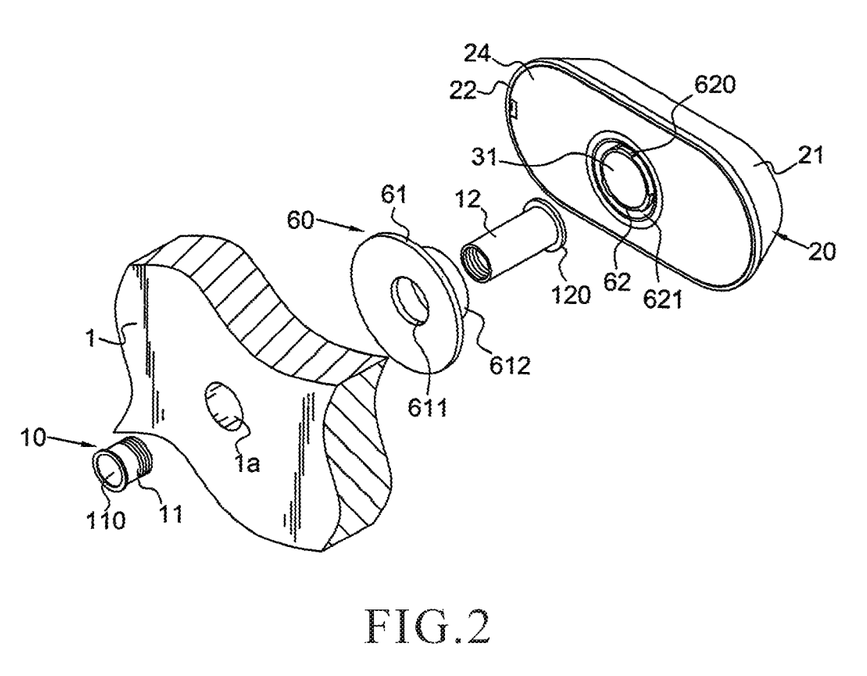
FIG. 2 is a perspective exploded view from another viewing angle, which schematically shows a digital peephole viewer according to the present invention.
Figure 3:
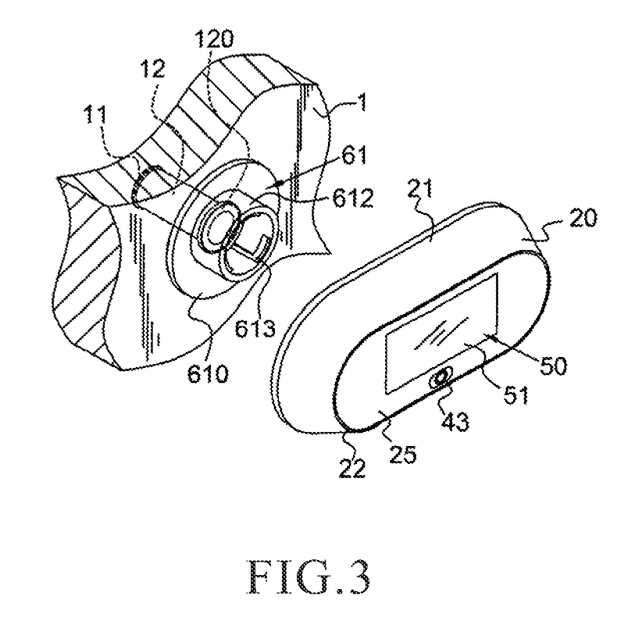
FIG. 3 is a partial perspective view schematically showing a semi-assembly of a digital peephole viewer according to the present invention.
Figure 4:
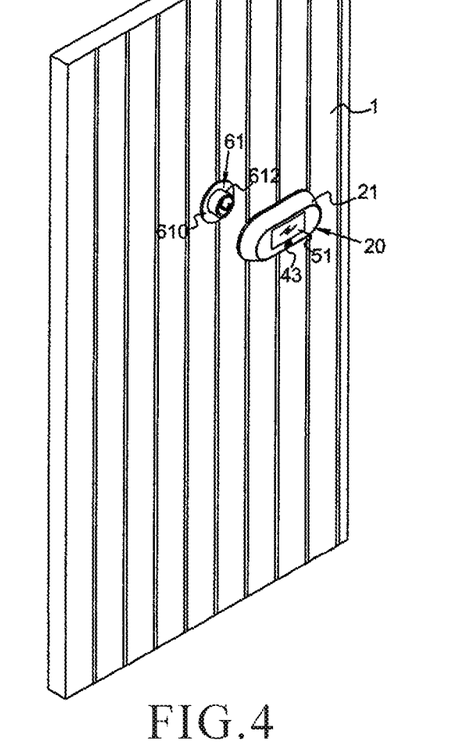
FIG. 4 is an overall perspective view schematically showing a semi-assembly of a digital peephole viewer according to the present invention.
Figure 5:
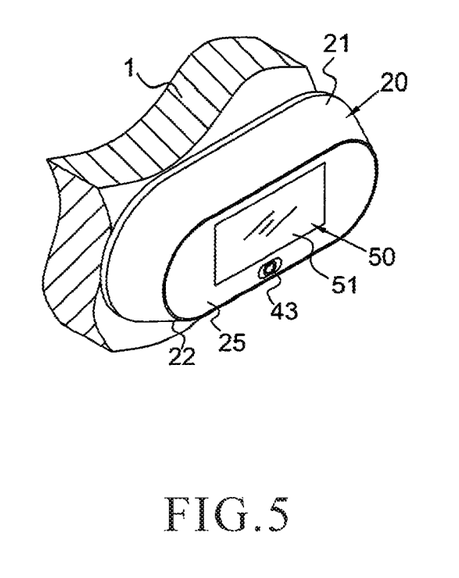
FIG. 5 is a partial perspective view schematically showing an assembly of a digital peephole viewer according to the present invention.
Figure 6:
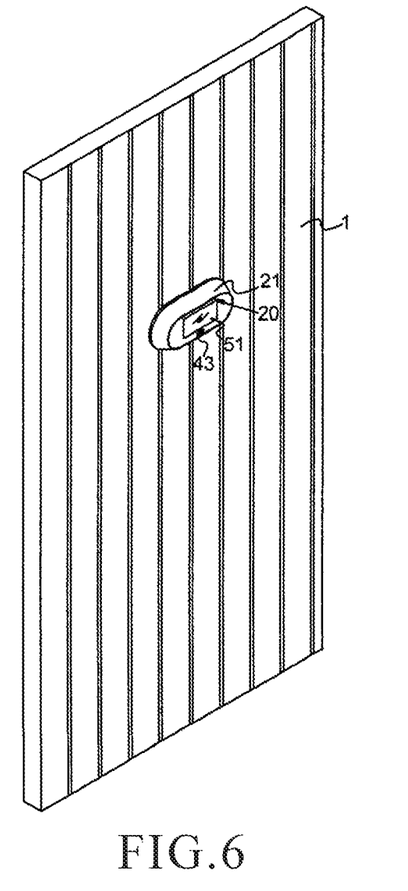
FIG. 6 is an overall perspective view schematically showing an assembly of a digital peephole viewer according to the present invention.

Refer to FIG. 1 and FIG. 2. In a third embodiment of the housing 20, the housing 20 includes a casing 21 having a first opening 22 and a second opening 23. A cover 24 is used to cover the first opening 22. The casing 21 accommodates the power supply unit 70. The user can open the cover 24 to replace the power supply unit 70. The display 51 of the display unit 50 is installed in the second opening 23, and a transparent plate 25 is used to cover the second opening 23 and protect the display 51.

2.4 Image Capture Unit

Figure 7:
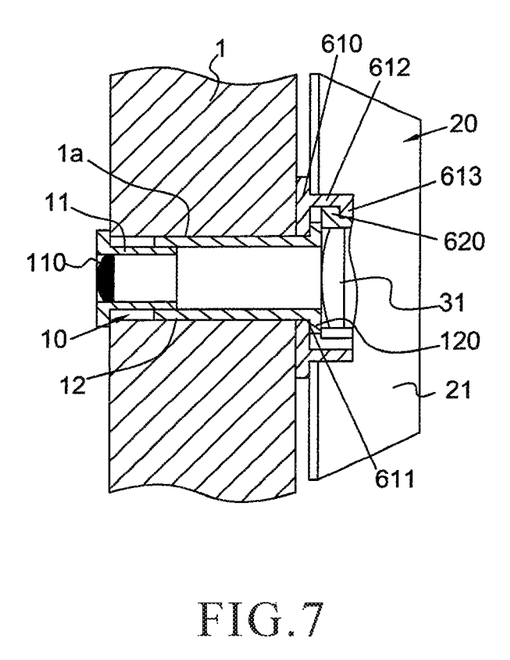
FIG. 7 is a sectional view schematically showing an assembly of a digital peephole viewer according to the present invention.
Figure 8:
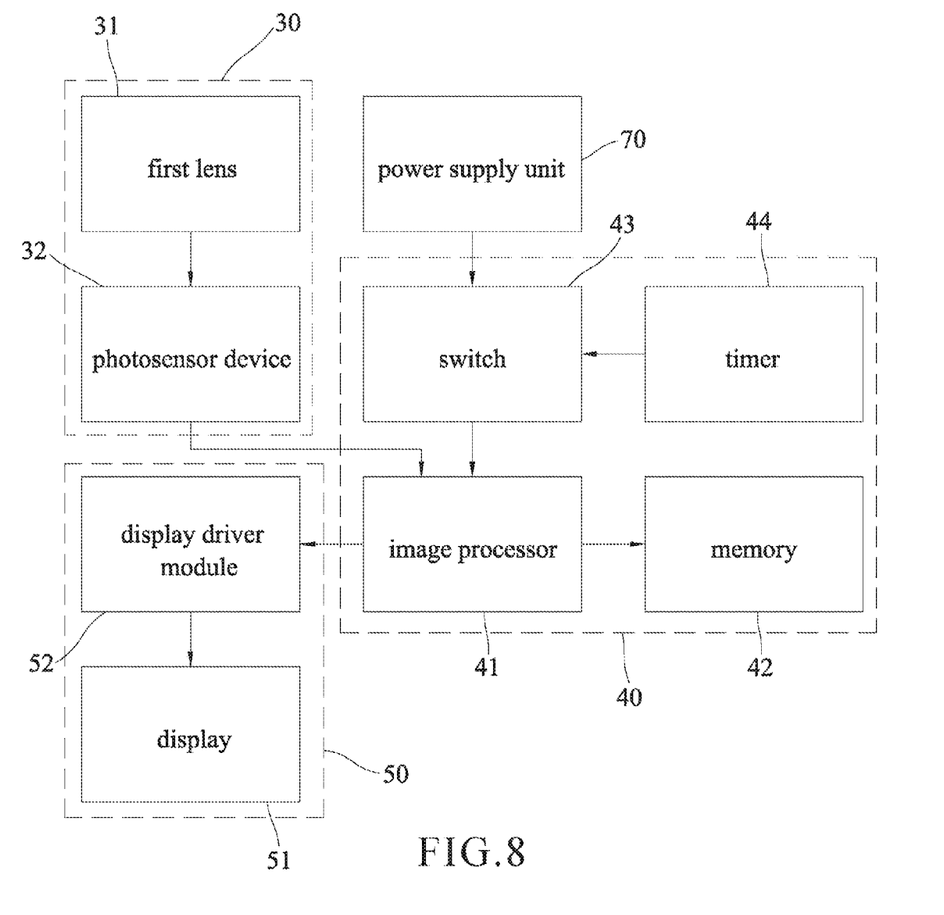
FIG. 8 is a block diagram schematically showing a circuitry of a digital peephole viewer according to the present invention.

Refer to FIG. 2, FIG. 7 and FIG. 8. The image capture unit 30 includes a first lens 31 arranged in the pipe 62 and a photosensor device 32, such as a CCD or CMOS device. Optical signals reach the photosensor device 32 via the light path of the second lens 110 of the door lens assembly 10 and the first lens 31. The photosensor device 32 converts the optical signals into an array of electronic signals. To achieve a better focusing effect, the axis of the door lens assembly 10 coincides with the axis of the first lens 31, and the photosensor device 32 is fixed on the focal plane of the lens.

2.5 Signal Processing Unit

Refer to FIG. 8. The signal processing unit 40 functions as the core of image processing and includes an image processor 41 electrically connected with the photosensor device 32. The image processor processes the arrayed electronic signals generated by the photosensor device 32 into the image signals of the AVI or MPEG-2 format.

In one embodiment of the signal processing unit 40, the image processor 41 has a built-in image processing software functioning as an image correction unit. The image processing software corrects the distorted image from the door lens assembly 10 and then sends the data to a memory 42 or the display unit 50. The display unit 50 is installed in the housing 20 and integrated with the structure of the housing 20. The display unit 50 includes a liquid crystal display 51 and a display driver module 52. The display driver module 52 converts the image signals into the signals for the display 51, and the display 52 presents realtime and dynamic images.

For power-saving and environmental protection, the digital peephole viewer device of the present invention is in a sleep mode normally and wakened up if necessary. To achieve the abovementioned objective, the housing 20 has a switch 43 electrically connected with the signal processing unit 40 and a timer 44 electrically connected with the switch 43. In another embodiment, the switch 43 itself has a timer function.

Once the switch 43 is turned on, the signal processing unit 40 enables the image capture unit 30 to capture the external images. At the same time, the timer 44 begins to count time. After the preset time interval has elapsed, the timer 44 disconnects the switch 43. Thereby, the signal processing unit 40 turns off the image capture unit 30 and display unit 50.

3. Operation of the Present Invention

Refer to FIG. 2, FIG. 7 and FIG. 8. When there is no visitor or incident, the image capture unit 30 and the display unit 50 stay in a sleep mode. When there is a visitor or an incident, the host goes to the door board 1 and presses the switch 43 on the housing 20 to trigger the signal processing unit 40. The signal processing unit 40 controls the image capture unit 30 to capture the external images.

The second lens 110 of the door lens assembly 10 and the first lens 31 capture the external images. The photosensor device 32 converts the optical images into arrayed electronic signals. The image processor 42 processes the arrayed electronic signals into continuous dynamic images of the AVI or MPEG-2 format. The image correction unit corrects the distorted images. Then, the display unit 50 on the housing 20 presents the continuous dynamic images. Thereby, the host can easily watch the images of the outside in real time.

Refer to FIG. 8. When the switch 43 is turned on, the timer 44, which is connected with the switch 43, begins to count time. When the preset time interval has elapsed, the timer 44 disconnects the switch 43. Then, the signal processing unit 40 turns off the image capture unit 30 and display unit 50. Thus, the image capture unit 30 and display unit 50 are restored to the sleep mode.

4. Conclusion

The digital peephole viewer device of the present invention can integrate with a commercially-available door lens assembly without developing any new mold to fabricate additional components of the existing door lens assembly. Therefore, the present invention can reduce the fabrication cost. The digital peephole viewer device of the present invention can convert the optical images of the outside into instant digital images to achieve a larger picture and a higher recognizability, whereby the host can easily watch the visitor or the external situation.

The embodiments described above are only to exemplify the present invention but not to limit the scope of the present invention. Any equivalent modification or variation according to the contents, characteristics and spirits of the present invention is to be also included within the scope of the present invention. The like object of the present invention has not yet appeared in papers, documents or markets. The present invention also possesses utility and non-obviousness. Therefore, the present invention meets the condition for a patent. Thus, the Inventor files the application for a patent. It will be appreciated if the patent is approved fast.

What is claimed is:

1. A digital peephole viewer device, which integrates with a door lens assembly on a door board, receives optical images from said door lens assembly, converts said optical images into digital images and presents said digital images, comprising a housing;
   an image capture unit installed in said housing and including a first lens receiving optical images captured by said door lens assembly;
   a signal processing unit converting said optical images into digital images and outputting said digital images;
   a display unit receiving said digital images and presenting said digital images; and
   a connection means integrating said housing and said door lens assembly wherein said door lens assembly includes a first tube and a second tube, which are coupled to each other in a screwing way; said first tube has a second lens; a first end of said second tube has an expanded rim; said first tube is inserted into one end of a through-hole of said door board; a second end of said second tube is inserted into the other end of said through-hole and coupled to said first tube in a screwing way; said connection means includes
      a seat having a plate with a through-hole, wherein said second tube is inserted through said through-hole to integrate with said first tube in a screwing way, wherein said expanded rim of said second tube is blocked by a perimeter of said through-hole; an annular wall projects from one side of said plate and surrounds said through-holes; an inner surface of said annular wall has several first tenons; and
      a pipe arranged in said housing and accommodating said first lens of said image capture unit, wherein an outer surface of said pipe has several second tenons corresponding to said first tenons, and
   wherein said expanded rim of said second tube clamps said seat to said door board when said first tube and said second tube are coupled to each other in a screwing way; one end of said pipe is inserted into said annular wall, and said first lens is aligned to one end of said second tube, and said pipe is rotated to an angle where said second tenons mate with said first tenons, whereby said housing is integrated with said seat and fixed on said door board.

2. The digital peephole viewer device according to claim 1, wherein one end of said pipe is trimmed to be coplanar with said housing; a rim of said pipe has an annular trench to receive said annular wall.

3. The digital peephole viewer device according to claim 1, wherein said housing has a cone-like appearance; one side of said housing having a larger area is faced to said door board, and another side of said housing having a smaller area accommodates a display of said display unit.

4. The digital peephole viewer device according to claim 1, wherein said housing includes a casing having a first opening, and a cover is used to cover said first opening; said casing accommodates a power supply unit; a user can open said cover to replace said power supply unit.

5. The digital peephole viewer device according to claim 1, wherein said housing includes a casing having a second opening; a display of said display unit is installed in said second opening.

6. The digital peephole viewer device according to claim 5, wherein a transparent plate is used to cover said second opening and protect said display.

7. The digital peephole viewer device according to claim 1, wherein said housing includes a casing having a first opening on one side thereof and a second opening on another side thereof; a cover is used to cover said first opening; said casing accommodates a power supply unit; a user can open said cover to replace said power supply unit; a display of said display unit is installed in said second opening.

8. The digital peephole viewer device according to claim 7, wherein a transparent plate is used to cover said second opening and protect said display.

9. The digital peephole viewer device according to claim 1, wherein said housing has a switch used to trigger said signal processing unit; when triggered, said signal processing unit controls said image capture unit to capture images and controls said display unit to present images.

10. The digital peephole viewer device according to claim 1, wherein said display unit is installed in said housing and integrated with structure of said housing; said display unit includes a liquid crystal display.

11. The digital peephole viewer device according to claim 1, wherein said signal processing unit includes an image correction unit; said image correction unit corrects images from said door lens assembly; said display unit presents images corrected by said image correction unit.

12. The digital peephole viewer device according to claim 1 further comprising a memory for recording images.

13. A digital peephole viewer device, which integrates with a door lens assembly on a door board and receives optical images from said door lens assembly, wherein said door lens assembly includes a first tube and a second tube, which are coupled to each other in a screwing way; said first tube has a second lens; a first end of said second tube has an expanded rim; said first tube is inserted into one end of a through-hole of said door board; a second end of said second tube is inserted into the other end of said through-hole and coupled to said first tube in a screwing way, and wherein said digital peephole viewer device comprises
- a housing having a first opening on one side thereof and a second opening on another side thereof, wherein a cover is used to cover said first opening, and a user can open said cover to replace a power supply unit arranged thereinside;
- an image capture unit installed in said housing and including a first lens receiving optical images captured by said door lens assembly;
- a signal processing unit converting said optical images into digital images and outputting said digital images;
- a display unit receiving said digital images, presenting said digital images, and including a display installed in said second opening of said housing; and
- a connection means integrating said housing and said door lens assembly and including
  - a seat having a plate with a through-hole, wherein said second tube is inserted through said through-hole to integrate with said first tube in a screwing way, wherein said expanded rim of said second tube is blocked by a perimeter of said through-hole; an annular wall projects from one side of said plate and surrounds said through-holes; an inner surface of said annular wall has several first tenons; and
  - a pipe arranged in said housing and accommodating said first lens of said image capture unit, wherein an outer surface of said pipe has several second tenons corresponding to said first tenons, and wherein one end of said pipe is trimmed to be coplanar with said housing, and wherein a rim of said pipe has an annular trench to receive said annular wall, and
- wherein said expanded rim of said second tube clamps said seat to said door board when said first tube and said second tube are coupled to each other in a screwing way; one end of said pipe is inserted into said annular wall, and said first lens is aligned to one end of said second tube, and said pipe is rotated to an angle where said second tenons mate with said first tenons, whereby said housing is integrated with said seat and fixed on said door board.

14. The digital peephole viewer device according to claim 13, wherein said signal processing unit includes an image correction unit; said image correction unit corrects images from said door lens assembly; said display unit presents images corrected by said image correction unit.

* * * * *